United States Patent
Vora

[11] 3,956,416
[45] May 11, 1976

[54] ALKYLATION PROCESS UTILIZING HF REGENERATOR STREAM TO A MULTI-TRAY ISOPARAFFIN STRIPPER

[75] Inventor: Bipin V. Vora, Buffalo Grove, Ill.

[73] Assignee: Universal Oil Products Company, Des Plaines, Ill.

[22] Filed: Dec. 16, 1974

[21] Appl. No.: 533,421

[52] U.S. Cl. .......................................... 260/683.48
[51] Int. Cl.² ........................................... C07C 3/54
[58] Field of Search .............................. 260/683.48

[56] References Cited
UNITED STATES PATENTS

| | | | |
|---|---|---|---|
| 3,410,759 | 11/1968 | Fontenot et al. | 260/683.48 |
| 3,478,125 | 11/1969 | Chapman | 260/683.48 |
| 3,763,265 | 10/1973 | Hutson, Jr. et al. | 260/683.48 |

Primary Examiner—Delbert E. Gantz
Assistant Examiner—G. J. Crasanakis
Attorney, Agent, or Firm—James R. Hoatson, Jr.; Thomas K. McBride; William H. Page, II

[57] ABSTRACT

In prior art HF alkylation processes, an HR regenerator overhead vapor stream is processed in various ways including combining it with overhead vapor streams of an isoparaffin stripper or an HF stripper, or condensing, settling, and pumping it in a regenerator overhead system to an HF alkylation reaction zone. In the present HF alkylation system comprising a reaction and settling zone, an acid regeneration zone, and a products fractionation zone including an isoparaffin stripper from which a side-cut recycle stream containing principally isoparaffin is withdrawn, an improvement is made by taking overhead vapor from the regenerator and introducing the vapor directly into the isoparaffin stripper at a locus above that at which the side-cut recycle stream is withdrawn.

2 Claims, 1 Drawing Figure

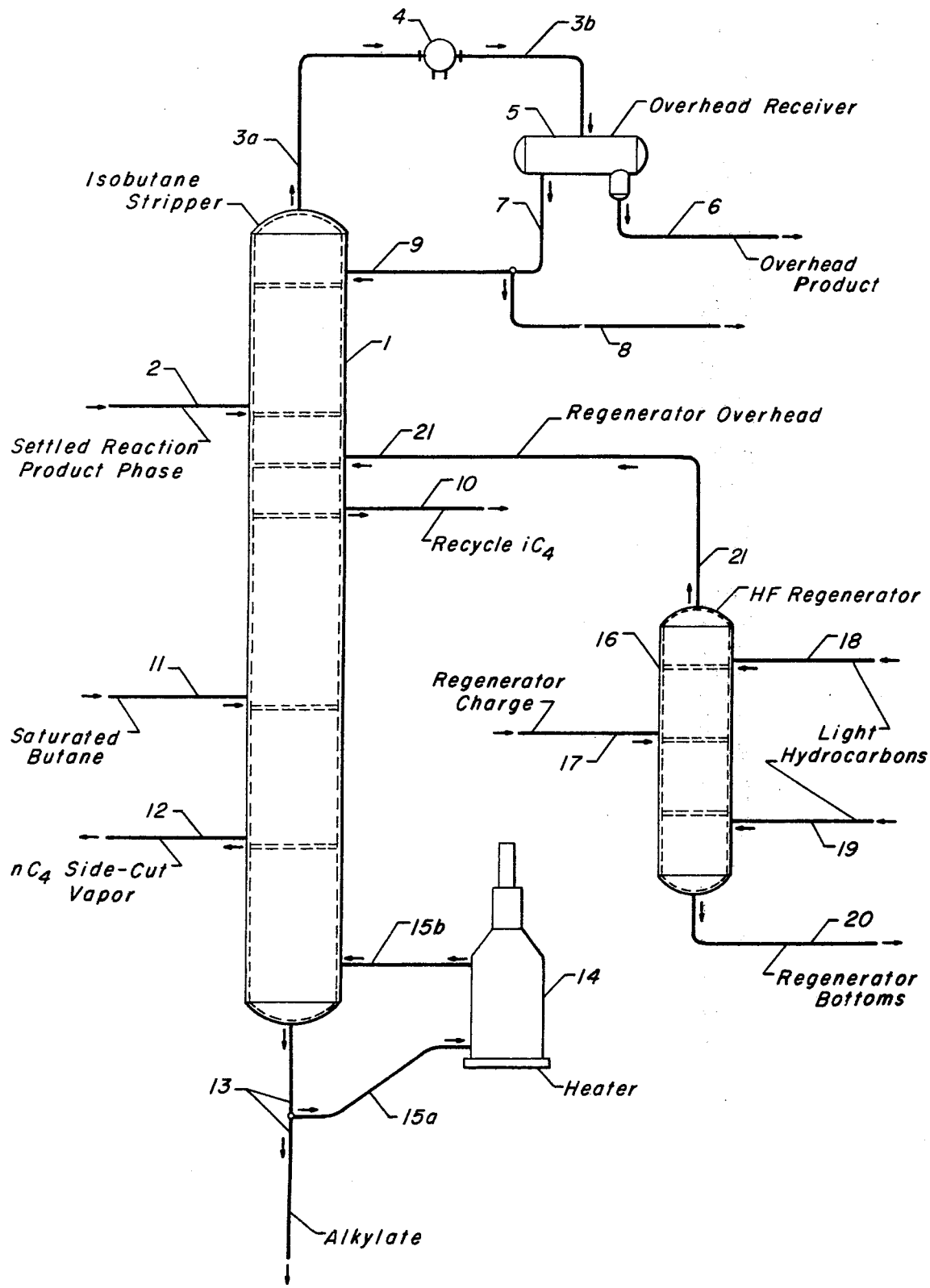

ALKYLATION PROCESS UTILIZING HF REGENERATOR STREAM TO A MULTI-TRAY ISOPARAFFIN STRIPPER

BACKGROUND OF THE INVENTION

This invention relates to a catalytic alkylation process. It particularly relates to an improved process for the separation of the hydrocarbon and acid components present in the effluent from a catalytic alkylation zone. It specifically relates to an improvement to eliminate the overhead vapor apparatus of the HF regenerator, including the overhead condenser, overhead receiver, and overhead pump.

It is well known in the prior art that catalytic alkylation using hydrofluoric acid or sulfuric acid as the catalyst has become an important chemical tool for preparing alkylated hydrocarbons and derivatives thereof. The commercial and industrial demand for these products is exemplified with the demand for isoparaffin hydrocarbons and alkyl-substituted benzenes of gasoline boiling range and with the demand for alkyl-substituted aromatics suitable for conversion to surfactants, e.g., detergents, wetting agents, etc. The prior art process of alkylation generally is effected by contacting an isoparaffin hydrocarbon feed stock with an olefin hydrocarbon in the presence of a catalyst such as hydrofluoric acid in a suitable reaction vessel for conducting chemical reactions.

In practice, there have been numerous process schemes advanced by the prior art for accomplishing the alkylation reaction, but it is extremely difficult to achieve a process scheme which embodies all of the desirable features of a completely optimum reaction. Optimizing the alkylation reaction is complicated by the fact that the alkylation reaction if not carried out properly has many side reactions, such as polymerization, which destroys the effectiveness of the reaction and inhibits the production of commercial quantities of desired alkylate. Additionally, the reaction, in order to be carried out commercially, requires a tremendous amount of auxiliary equipment for the recovery of the alkylate product, for the regeneration and reuse of the excess catalyst, and for the recovery and reuse of the excess reactants which have passed through the reaction system.

The catalytic alkylation process to which the present invention is applicable consists of a process in which a mixture of hydrocarbons containing isoparaffins such as isobutane, isopentane, and the like, and olefins such as propylene, butenes, isobutenes, and the like, are mixed intimately in the presence of a strong acid catalyst, such as hydrofluoric acid or sulfuric acid at generally room temperature or lower for sufficient time to complete the reaction. The effluent from the reaction zone contains saturated isoparaffin hydrocarbons of higher molecular weight or boiling point than the isoparaffin in the original mixture. For convenience, these higher molecular weight isoparaffin hydrocarbons which comprise the reaction product from the alkylation zone are called "alkylate." Isobutane has been used almost exclusively because of its reactivity and availability to produce high quality alkylate product. In similar manner, among the olefins, butenes and propylenes have been used satisfactorily. In some cases it is desirable to use solely propylene or butene as the olefin reactant.

As is typical in most commercial chemical plants, the reaction between the isoparaffin hydrocarbon and the olefin hydrocarbon is performed with an excess of isoparaffin in the reaction zone. Accordingly, there is a large excess of the isoparaffin hydrocarbon remaining in the effluent from the reaction zone. Additionally, there is a significant quantity of $C_3$ hydrocarbons which pass through the system, and for economy sake, must be recovered in as high yield as possible. In similar manner, it is desirable to recover for reuse the isoparaffin reactant in as high yield as possible, which is accomplished in an isoparaffin stripper, or, more specifically when isobutane is the isoparaffin, an isostripper.

In processes of the type referred to above there is also a need for periodic regeneration of the catalyst system. This is usually accomplished by prior art schemes by taking a stream of at least a portion of the acid catalyst, e.g., hydrofluoric acid, and passing it to a regeneration column wherein the regenerated catalyst is stripped with a light hydrocarbon, for example, hot or superheated vaporous isobutane. The purpose of this regeneration is to remove from the catalyst impurities such as water and acid soluble oils which accumulate in the system. These oils are of a polymeric composition which is in equilibrium with the alkylate hydrocarbon and heavy tar produced in the alkylation reaction. As used in this specification, these impurities and/or contaminants in the catalyst phase are for convenience lumped together and characterized as being material boiling above the boiling point of hydrogen fluoride acid.

The prior art processes for regenerating liquid catalyst such as hydrofluoric acid catalyst usually involve distillation schemes which present problems both from a process standpoint and from an apparatus standpoint. For example, since it is an acid system, the presence of water will cause severe corrosion problems in the regeneration column and in any condensing means associated therewith. Expensive, high quality alloy metallurgy is provided in the various apparatus associated with the regenerator to reduce the rate of corrosion found in this system, and even so, frequent replacement of equipment is not unusual. In addition, sufficient heat must be applied to the catalyst stream in order to vaporize the catalyst for recovery as a purified product. However, in the vaporization of this catalyst stream there will remain a non-vaporized residue of heavy organic diluent which tends to foul the tubes of the heat inducing means. Another problem present in the prior art process is the difficulty of providing sufficient stripping media so that the acid losses to the tar residue are minimized. If sufficient stripping media is passed into the regeneration column so that no acid will remain in the bottom product, there is frequently entrained overhead an excessive portion of heavy organic diluent which then contaminates the vaporized catalyst stream thereby creating additional fouling problems in the lines and condensing means associated with the regeneration system.

In the prior art, several means have been used to eliminate the HF regenerator overhead system, which can be described as the overhead condenser, overhead receiver, and overhead pump, or to combine that system with the overhead system of another fractionation apparatus. Thus it is seen in U.S. Pat. No. 3,349,146 that the regenerator overhead system is combined with the overhead system of a fractionator which strips HF from propane. Also in the prior art, in an isobutane stripper system wherein isobutane recycle is withdrawn from the isobutane stripper system as condensed overhead vapor saturated with HF, the overhead vapors of the HF regenerator are introduced into the overhead vapor conduit of the isobutane stripper upstream of the overhead condenser, thereby eliminating the regenerator overhead system. However, in the modern isobutane stripper, recycle isobutane is withdrawn as a side-cut from the isobutane stripper, and all overhead hydrocarbon product is withdrawn as feed to subsequent fractionation, i.e., depropanization. When the modern isobutane stripper came into use, it was considered desirable to separate the overhead systems of the regenerator and isobutane stripper in an effort to reduce incremental capital and operating costs of the depropanization fractionation, which were deemed greater than the incremental capital and operating costs of the separate regenerator overhead system.

SUMMARY OF THE INVENTION

Accordingly, it is an object of the present invention to provide an improvement in the regeneration of spent acid alkylation catalyst and an improvement in the fractionation of alkylation products.

It is a specific object of this invention to provide an improvement for regeneration of HF catalyst in a more economical and facile manner.

The embodiment of the invention is: In a process for producing an alkylation reaction product from an isoparaffin reactant and an olefin-acting reactant utilizing hydrogen fluoride catalyst wherein said reactants and said catalyst are admixed in a reactor at alkylation conditions; a reactor effluent is settled to form a settled catalyst phase containing acid soluble oils and a settled reaction product phase containing unreacted isoparaffin; at least a portion of said settled reaction product phase is introduced into a multi-tray isoparaffin stripper at an intermediate locus in the column and a side-cut recycle stream containing isoparaffin reactant is withdrawn from said multi-tray isoparaffin stripper at a locus below the inlet locus of said settled reaction product phase; at least a portion of said settled catalyst phase is introduced into a catalyst regenerator where a light hydrocarbon is used to strip hydrogen fluoride from acid soluble oils at regeneration conditions, acid soluble oils are removed from a lower part of said regenerator, and stripped hydrogen fluoride and said light hydrocarbon are withdrawn as a regenerator overhead vapor stream from an upper part of said regenerator; the improvement comprising passing said regenerator overhead vapor stream from said regenerator into said multi-tray isoparaffin stripper at a locus above said locus at which said side-cut recycle stream is withdrawn.

A specific embodiment of this invention includes the improvement described hereinabove wherein isobutane is the isoparaffin reactant and the olefin-acting reactant is a mono-olefin having from 3 to 5 carbon atoms per molecule.

Another specific embodiment of this invention includes the improvement described above wherein said vapors from said regenerator is introduced into said multi-tray isoparaffin stripper at a locus between the locus at which said settled reaction product phase is introduced and said locus at which said side-cut recycle stream is withdrawn.

The description of the present invention will be limited to the processing scheme for handling the effluent from a conventional isobutane/mixed olefin alkylation reaction zone, although the scope of the invention is not necessarily to be limited thereto. The effluent is prepared by means known to those skilled in the art, and generally, comprises the steps of commingling an olefin-containing feedstock with an isobutane-containing feed stock and passing the mixture into a conventional alkylation reaction zone. An isobutane-rich recycle stream is also added to the reaction zone in order that the isobutane to olefin mol ratio in the presence of the catalyst is maintained at the proper level. Means for removing the heat of reaction from the reaction zone must be provided and the contact time in the reactor is maintained for a period sufficient to intimately mix and contact the feed mixture with the catalyst so that the alkylation reaction can occur. The total effluent from the reaction zone is generally removed and passed into a separation means whereby an acid phase containing acid soluble oils is separated from a hydrocarbon reaction product phase, generally by settling. The acid is returned to the reactor, preferably by gravity flow in admixture with fresh acid, as needed, and the hydrocarbon reaction product phase is further processed as described hereinbelow. A portion of the acid phase is also passed to a regeneration zone by this invention in conjunction with the process of the hydrocarbon phase.

Conventional alkylation conversion conditions of temperature, pressure, isobutane-olefin mol ratio, and hydrogen fluoridehydrocarbon volume ratio, can be employed advantageously in the reaction zone. For example, the alkylation of isobutane with a feed comprising propylene and butenes can be carried out at temperatures between 0°F. and 140°F., preferably between 80°F. and 110°F., at pressures sufficiently high to keep the hydrocarbons and catalyst in liquid phase, and at isobutane-olefin mol ratios between 2:1 and 20:1, preferably between 10:1 and 15:1. Ratios of isobutane-olefin of at least 2:1 are essential since lower ratios tend to cause polymerization of the olefins with resulting decrease in yield of desirable alkylate product. The volume ratio of catalyst to hydrocarbon charge can be varied considerably. For example, a ratio of 1:1 to 10:1 can be used, preferably at least 2:1 is used. The acid catalyst charged to the reactor can be substantially anhydrous hydrogen fluoride and can have a titratable acidity as low as 65% by weight, but preferably is maintained between 85% and 95% acidity.

As will become more evident from a detailed description of the present invention with reference to the appended drawing, operating in the manner generally described hereinabove and utilizing the improvement of the present invention will produce an alkylate product having an end point below 400°F. and an unleaded Research Octane Number of at least 92 with a hydrogen fluoride catalyst consumption generally of less than 0.2 pounds of catalyst per barrel of alkylate produced. Additionally, significant economy of operation is achieved over the process schemes taught by the prior art.

As previously mentioned, hydrocarbons substantially free from a major proportion of hydrogen fluoride catalyst are withdrawn from the settler vessel associated with the alkylation reaction zone, and are introduced as a settled reaction product phase into an isobutane stripper. The isobutane stripper operates as a fractionation column and accomplishes a substantial separation between propane, lower boiling isobutane, higher boiling n-butane, and reactor effluent product, namely, alkylate.

Frequently, a saturated butane stream including isobutane is available within a refinery from another processing unit. The isobutane in such a saturated butane stream is a desirable feed to an alkylation reaction system, however, it is often beneficial to make a separation of the isobutane from n-butane prior to introducing such a stream to the alkylation reaction zone. For this reason, a saturated butane stream is often introduced as a secondary inlet stream to the isobutane stripper of an alkylation unit, and the n-butane in that stream plus whatever n-butanes are present in the settled reaction product phase are removed from the alkylation unit by withdrawing a side-cut vapor product stream containing principally n-butane at the proper locus of the isobutane stripper. Normally the isobutane stripper is controlled in such a manner so as to obtain a desired vapor pressure of the alkylate product stream, which is withdrawn from the bottom. The isobutane in the saturated butane stream principally is withdrawn from the isobutane stripper in a side-cut recycle stream which is passed to the alkylation reaction zone, but a small amount may also be withdrawn in an overhead product stream and the principally n-butane side-cut vapor product stream. The side-cut recycle stream principally contains unreacted isobutane introduced into the isobutane stripper as part of the settled reaction product phase and the isobutane portion of the saturate butane feed stream.

The isobutane stripper overhead vapors are condensed and cooled to about 60° to 140°F., introduced into an overhead receiver, and separated into a settled acid phase and a settled hydrocarbon overhead phase, saturated with HF. The settled acid phase is withdrawn from the overhead receiver, and passed to the reaction zone. The settled hydrocarbon overhead phase consisting principally of isobutane and propane is withdrawn from the overhead receiver, an aliquot portion is passed to the top of the isobutane stripper as reflux, and a second aliquot portion is taken as an overhead product stream and passed to further fractionation, i.e., a depropanizer, to separate a final product stream consisting principally of propane from the isobutane stripper overhead product stream. The depropanizer apparatus must be adequately sized to handle not only the propane in the isobutane stripper overhead product stream, but also the isobutane and other heavier components which constitute a major portion of the stream. Therefore, to minimize capital and operating costs of the depropanizer apparatus, it is important to maximize the propane purity of the isobutane stripper overhead product stream.

It has been found desirable to minimize the HF content of the side-cut recycle stream to the alkylation zone for the purpose of improving alkylate quality. For this and other reasons, the modern isobutane stripper has been designed with recycle isobutane as a vapor side-cut stream. When withdrawn at a suitable locus of the isobutane stripper below the feed tray, the side-cut recycle stream when condensed and cooled to alkylation reaction temperatures will contain less than saturation quantity of HF and about 60 to 95 weight percent isobutane. When compared with recycle isobutane withdrawn as an overhead stream from an isobutane stripper, recycle isobutane withdrawn as a side-cut stream will contain less HF and less propane, which is considered beneficial to higher alkylate quality and lower capital and operating costs.

The HF regenerator design is familiar to one skilled in the art. A portion of the HF acid containing acid soluble oils is withdrawn from the reactor/settler system and introduced directly or heated to about 150° to 300°F. and introduced into the regenerator at about the middle tray. A cooled light hydrocarbon liquid stream at about 80° to 150°F. is introduced as reflux above the top tray of the regenerator and a superheated light hydrocarbon vapor stream at about 300 to 500°F. is introduced below the bottom tray. The cooled light hydrocarbon liquid stream and superheated light hydrocarbon vapor stream contain principally isobutane and are withdrawn from the bottom section of the depropanizer as liquid and vapor streams, respectively. The trays of the regenerator may be sieve type or valve type. Liquid acid soluble oils are withdrawn from the regenerator bottom at a temperature of about 350°F. and a regenerator overhead vapor stream of HF and hydrocarbon containing mostly isobutane is withdrawn from the top at about 150° to 200°F. and a pressure of about 100 to 200 psig. The disposition of the regenerator overhead vapor stream is the subject of the present invention. In the prior art, said regenerator overhead vapor stream is combined with the overhead stream of a fractionator stripping HF from propane or the overhead stream of an isobutane stripper, or condensed, cooled, and passed to the alkylation reaction zone, etc. In the present invention, the regenerator overhead vapor stream is introduced into the isobutane stripper at a locus above the locus at which the side-cut isobutane recycle stream is withdrawn, and in a preferred embodiment, below the locus at which the settled reaction product phase is introduced into the isobutane stripper. The HF in the regenerator overhead vapor stream is principally withdrawn from the isobutane stripper as part of the overhead vapor stream, condensed, and passed to the reaction zone as HF liquid, while the hydrocarbon in the regenerator overhead vapor stream is withdrawn from the isobutane stripper principally in the side-cut recycle isobutane stream. As compared to introducing a regenerator overhead vapor stream into an isobutane stripper overhead vapor stream, the practice of the present invention will reduce the isobutane concentration of the isobutane stripper settled hydrocarbon overhead phase and result in lower capital and operating costs of the isobutane stripper-depropanizer fractionation systems, at the same time maintaining HF in the side-cut isobutane recycle stream below the saturation point of HF when the recycle stream is cooled to alkylation reaction temperature. The isobutane separation described above is accomplished by the fractionation which occurs between the top of the isobutane stripper and the locus at which the regenerator overhead vapor stream is introduced into the isobutane stripper, resulting in a substantial portion of the isobutane in that stream passing into the side-cut recycle isobutane stream while a relatively small portion passes into the isobutane stripper overhead vapor stream and subsequently into the overhead product stream.

DESCRIPTION OF THE DRAWING

An understanding of this invention may be aided by reference to the accompanying drawing which represents a schematic flow diagram of an embodiment of the invention.

Many variations and modifications within the scope of this invention will be obvious to one skilled in the art from the description herein provided. Alkylation reaction zone effluent is separated to form a hydrocarbon settled reaction product phase stream which is introduced as a feed into an isobutane stripper 1 via conduit 2. An overhead vapor stream is withdrawn via conduit 3a, condensed and cooled in exchanger 4 and introduced via conduit 3b into overhead receiver 5. A settled acid phase and a settled hydrocarbon overhead phase are separated in overhead receiver 5. The settled acid phase is withdrawn via conduit 6 and passed to the reaction zone. The settled hydrocarbon overhead phase is withdrawn via conduit 7, a first portion passing as an overhead product stream to depropanization via conduit 8, and a second portion passing to the top of the isobutane stripper as reflux via conduit 9. At a tray below the feed tray, a side-cut recycle stream containing principally isobutane is withdrawn via conduit 10. A saturated butane stream is introduced into isobutane stripper 1 via conduit 11, a principally n-butane side-cut vapor stream is withdrawn via conduit 12, and an alkylate product stream is withdrawn from the bottom via conduit 13. Heat is supplied to the isobutane stripper by heater 14 in bottoms conduits 15a and 15b.

Simultaneous with the operation of the isobutane stripper described hereinabove, a portion of HF acid containing acid soluble oils is withdrawn from a settled catalyst phase of the alkylation reaction zone effluent and introduced into regenerator 16 via conduit 17. A light hydrocarbon stream comprising essentially isobutane and originating in a depropanizer is introduced as a reflux liquid to the top of regenerator 17 via conduit 18, and a second light hydrocarbon stream of similar source and content is introduced as a stripping vapor below the bottom tray of the regenerator via conduit 19. Acid soluble oils are withdrawn via conduit 20 from the regenerator bottom. From the top of the regenerator, a regenerator overhead vapor stream containing stripped hydrogen fluoride and light hydrocarbon are withdrawn via conduit 21 and introduced into isobutane stripper 1 at a tray between the feed tray and the tray at which the side-cut recycle stream is withdrawn.

EXAMPLE

Shown herein below is a mol balance by component of the inlet and outlet streams of an isobutane stripper and an HF regenerator, for three cases with constant alkylation reaction conditions: (a) separate HF regenerator and isobutane stripper overhead vapor systems; (b) HF regenerator overhead vapor stream flows into isobutane stripper at a locus below the feed stream inlet and above the isobutane recycle stream withdrawal; (c) HF regenerator overhead vapor stream flows into isobutane stripper overhead vapor stream. For the isobutane stripper design with an isobutane recycle stream withdrawn as a side-cut stream, (b) is preferred over (a) because (b) eliminates the overhead condensation system of (a) with only a small increase in flow to the depropanizer. (b) is also preferred over (c) because (c) would result in greater flow to the depropanizer and accordingly (c) would require greater capital and operating expense.

(a) - SEPARATE REGENERATOR/ISOBUTANE STRIPPER - Mol/Hr.

| | Isobutane Stripper Charge | Saturated Butane Charge | Regenerator Charge | Depropanizer Charge | Isobutane Stripper Overhead HF Liquid | Isobutane Recycle | n-Butane Product | Alkylate Product | Lt. Hc. to Regenerator | Regenerator Overhead | Regenerator Bottoms |
|---|---|---|---|---|---|---|---|---|---|---|---|
| HF | 655 | — | 323 | 33 | 592 | 30 | — | — | — | 322 | 1 |
| $C_2$ | 3 | — | — | 3 | — | 0 | — | — | — | 0 | — |
| $C_3$ | 1,289 | 11 | — | 268 | — | 1,032 | — | — | 5 | 5 | — |
| $iC_4$ | 15,540 | 415 | — | 1,079 | — | 14,829 | 44 | 2 | 460 | 460 | — |
| $nC_4$ | 3,204 | 918 | — | 107 | — | 2,957 | 847 | 210 | 46 | 46 | — |
| $iC_5$ | 109 | 73 | — | — | — | 60 | 21 | 100 | — | — | — |
| $nC_5$ | 0 | 21 | — | — | — | 0 | 0 | 21 | — | — | — |
| $C_6+$ | 1,400 | 16 | — | — | — | 131 | 12 | 1,274 | — | — | — |
| Other | — | — | 5 | — | — | — | — | — | — | — | 5/6 |
| TOTAL | 22,200 | 1,454 | 328 | 1,490 | 592 | 19,039 | 924 | 1,607 | 511 | 833 | |

(b) - REGENERATOR OVERHEAD VAPOR TO ISOBUTANE STRIPPER - Mol/Hr.

| | Isobutane Stripper Charge | Saturated Butane Charge | Regenerator Charge | Depropanizer Charge | Isobutane Stripper Overhead HF Liquid | Isobutane Recycle | n-Butane Product | Alkylate Product | Lt. Hc. to Regenerator | Regenerator Overhead | Regenerator Bottoms |
|---|---|---|---|---|---|---|---|---|---|---|---|
| HF | 637 | — | 323 | 33 | 882 | 44 | — | — | — | 322 | 1 |
| $C_2$ | 3 | — | — | 3 | — | 0 | — | — | — | 0 | — |
| $C_3$ | 1,284 | 11 | — | 268 | — | 1,032 | — | — | 5 | 5 | — |
| $iC_4$ | 15,079 | 415 | — | 1,196 | — | 14,829 | 44 | 2 | 460 | 460 | — |
| $nC_4$ | 3,157 | 918 | — | 107 | — | 2,957 | 847 | 210 | 46 | 46 | — |
| $iC_5$ | 108 | 73 | — | — | — | 60 | 21 | 100 | — | — | — |
| $nC_5$ | 0 | 21 | — | — | — | 0 | 0 | 21 | — | — | — |
| $C_6+$ | 1,400 | 16 | — | — | — | 131 | 12 | 1,274 | — | — | — |
| Other | — | — | 5 | — | — | — | — | — | — | — | 5/6 |
| TOTAL | 21,668 | 1,454 | 328 | 1,607 | 882 | 19,053 | 924 | 1,607 | 511 | 833 | |

(c) - REGENERATOR OVERHEAD VAPOR TO ISOBUTANE STRIPPER OVERHEAD VAPOR - Mol/Hr.

| | Isobutane Stripper Charge | Saturated Butane Charge | Regenerator Charge | Depropanizer Charge | Isobutane Stripper Overhead HF Liquid | Isobutane Recycle | n-Butane Product | Alkylate Product | Lt. Hc. to Regenerator | Regenerator Overhead | Regenerator Bottoms |
|---|---|---|---|---|---|---|---|---|---|---|---|
| HF | 637 | — | 323 | 44 | 885 | 30 | — | — | — | 322 | 1 |
| $C_2$ | 3 | — | — | 3 | — | 0 | — | — | — | 0 | — |
| $C_3$ | 1,284 | 11 | — | 273 | — | 1,027 | — | — | 5 | 5 | — |
| $iC_4$ | 15,080 | 415 | — | 1,540 | — | 14,369 | 44 | 2 | 460 | 460 | — |
| $nC_4$ | 3,158 | 918 | — | 153 | — | 2,911 | 847 | 210 | 46 | 46 | — |
| $iC_5$ | 108 | 73 | — | — | — | 60 | 21 | 100 | — | — | — |
| $nC_5$ | 0 | 21 | — | — | — | 21 | 0 | 21 | — | — | — |
| $C_6+$ | 1,400 | 16 | — | — | — | 131 | 12 | 1,274 | — | — | — |
| Other | — | — | 5 | — | — | — | — | — | — | — | 5/6 |
| TOTAL | 21,670 | 1,454 | 328 | 2,013 | 885 | 18,549 | 924 | 1,607 | 511 | 833 | |

I claim as my invention:

1. In a process for producing an alkylation reaction product from an isoparaffin reactant and an olefin-acting reactant utilizing hydrogen fluoride catalyst wherein said reactants and said catalyst are admixed in a reactor at alkylation conditions; a reactor effluent is settled to form a settled catalyst phase containing acid soluble oils and a settled hydrocarbon product phase containing unreacted isoparaffin; the improved method which comprises introducing at least a portion of said settled hydrocarbon product phase into a multi-tray isoparaffin stripper at an intermediate locus in the stripper, withdrawing a side-cut recycle stream containing isoparaffin reactant from said multi-tray isoparaffin stripper at a locus below the inlet locus of said settled reaction product phase; introducing at least a portion of said settled catalyst phase into a catalyst regenerator and therein contacting the catalyst phase at regeneration conditions with a light hydrocarbon to strip hydrogen fluoride from acid soluble oils, withdrawing acid soluble oils from a lower part of said regenerator, passing stripped hydrogen fluoride and said light hydrocarbon as a regenerator overhead vapor stream from an upper part of said regenerator to said multi-tray isoparaffin stripper at a locus below said intermediate locus at which said settled reaction product phase is introduced and above said locus at which said side-cut recycle stream is withdrawn.

2. The improved method of claim 1 wherein the isoparaffin reactant is isobutane and the olefin-acting reactant is a monoolefin having from 3 to 5 carbon atoms per molecule.

* * * * *